United States Patent
Kim et al.

(10) Patent No.: US 7,541,366 B2
(45) Date of Patent: Jun. 2, 2009

(54) PYRROLO[3,2-C]PYRIDINE DERIVATIVES AND PROCESSES FOR THE PREPARATION THEREOF

(75) Inventors: Jae-Gyu Kim, Seoul (KR); Byung-Nak Ahn, Seoul (KR); Hyouk-Woo Lee, Yongin (KR); Suk-Won Yoon, Seoul (KR); Young-Ae Yoon, Seoul (KR); Hyun-Ho Choi, Seoul (KR); Heui-Il Kang, Gunpo (KR)

(73) Assignee: YUHAN Corporation, Seoul (KR)

( * ) Notice: Subject to any disclaimer, the term of this patent is extended or adjusted under 35 U.S.C. 154(b) by 313 days.

(21) Appl. No.: 11/574,406

(22) PCT Filed: Sep. 3, 2005

(86) PCT No.: PCT/KR2005/002925

§ 371 (c)(1),
(2), (4) Date: Feb. 27, 2007

(87) PCT Pub. No.: WO2006/025715

PCT Pub. Date: Mar. 9, 2006

(65) Prior Publication Data

US 2007/0249658 A1    Oct. 25, 2007

(30) Foreign Application Priority Data

Sep. 3, 2004    (KR) ............... 10-2004-0070534

(51) Int. Cl.
*A61K 31/437*    (2006.01)
*C07D 471/04*    (2006.01)
(52) U.S. Cl. ........................... 514/300; 546/113
(58) Field of Classification Search ................ 546/113; 514/300

See application file for complete search history.

(56) References Cited

U.S. PATENT DOCUMENTS

| 4,450,164 | A | 5/1984 | Bristol et al. |
| 2004/0110785 | A1 | 6/2004 | Wang et al. |

FOREIGN PATENT DOCUMENTS

| WO | 02076963 | 10/2002 |
| WO | 03044015 | 6/2003 |
| WO | 03053970 | 7/2003 |

*Primary Examiner*—Patricia L Morris
(74) *Attorney, Agent, or Firm*—Sughrue Mion, PLLC

(57) ABSTRACT

The present invention provides novel pyrrolo[3,2-c]pyridine derivatives or pharmaceutically acceptable salts thereof, processes for the preparation thereof, and compositions comprising the same. The pyrrolo[3,2-c]pyridine derivatives or pharmaceutically acceptable salts thereof of the present invention have excellent proton pump inhibition effects and possess the ability to attain a reversible proton pump inhibitory effect.

7 Claims, No Drawings

PYRROLO[3,2-C]PYRIDINE DERIVATIVES AND PROCESSES FOR THE PREPARATION THEREOF

TECHNICAL FIELD

The present invention relates to novel pyrrolo[3,2-c]pyridine derivatives or pharmaceutically acceptable salts thereof which have an excellent inhibitory activity against gastric acid secretion, processes for the preparation thereof, and pharmaceutical compositions comprising the same.

BACKGROUND ART

Peptic ulcer disease occurs when offensive factors involving gastric acid secretion are strong or defensive factors of gastric mucous are weak. For the treatment of peptic ulcer disease, various drugs such as antacid, anticholinergic agent, $H_2$-receptor antagonist, and proton pump inhibitor have been used. The advent of omeprazole as a proton pump inhibitor has rekindled research activities in this field.

However, it has been pointed out that proton pump inhibition by omeprazole is irreversible, thereby incurring long-term inhibition of gastric acid secretion, which may induce side effects. Accordingly, various attempts to develop a reversible proton pump inhibitor are being made. For example, imidazopyridine derivatives are disclosed in WO 98/37,080 (AstraZeneca AB), WO 00/17,200 (Byk Gulden Lomberg Chem.), and U.S. Pat. No. 4,450,164 (Schering Corporation) as a reversible proton pump inhibitor. Further, pyrimidine derivatives are also disclosed in European Patent No. 775,120 (Yuhan Corp.).

DISCLOSURE OF INVENTION

Technical Problem

The present invention provides novel pyrrolo[3,2-c]pyridine derivatives or pharmaceutically acceptable salts thereof, which have excellent proton pump inhibition effects and possess the ability to attain a reversible proton pump inhibitory effect.

Technical Solution

According to an aspect of the present invention, there is provided a pyrrolo[3,2-c]pyridine derivative or a pharmaceutically acceptable salt thereof.

Further, according to another aspect of the present invention, there is provided a process for the preparation of the pyrrolo[3,2-c]pyridine derivative or a pharmaceutically acceptable salt thereof.

Further, according to another aspect of the present invention, there is provided a pharmaceutical composition comprising the pyrrolo[3,2-c]pyridine derivative or a pharmaceutically acceptable salt thereof as an active ingredient and a pharmaceutically acceptable carrier.

BEST MODE

In accordance with an aspect of the present invention, there is provided a compound of the formula (I) or a pharmaceutically acceptable salt thereof:

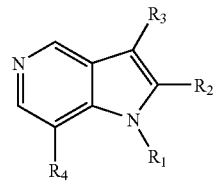

wherein:

$R_1$ is hydrogen; a straight or branched $C_1$-$C_6$ alkyl group, optionally substituted with one or more substituents selected from the group consisting of $C_1$-$C_5$ alkoxy, $C_3$-$C_7$ cycloalkyl, 1,3-dioxolanyl, cyano, naphthyl, $C_2$-$C_5$ alkenyloxy, and 2,3-dihydrobenzo[1,4]dioxinyl; a $C_2$-$C_6$ alkenyl group; a $C_2$-$C_6$ alkynyl group; or a benzyl group, optionally substituted with one or more substituents selected from the group consisting of halogen, $C_1$-$C_3$ alkyl, $C_1$-$C_3$ alkoxy, cyano, $C_1$-$C_3$ alkoxycarbonyl, and trifluoro-$C_1$-$C_3$ alkyl, $R_2$ is a straight or branched $C_1$-$C_6$ alkyl group, $R_3$ is hydrogen; a straight or branched $C_1$-$C_6$ alkyl group optionally substituted with hydroxyl or cyano, and $R_4$ is a 1,2,3,4-tetrahydroisoquinolinyl group optionally one or more substituted with halogen or $C_1$-$C_5$ alkyl a benzyloxy group optionally one or more substituted with halogen or $C_1$-$C_5$ alkyl; or a benzylamino group optionally substituted with halogen.

Among the compounds of the formula (I) or its pharmaceutically acceptable salt of the present invention, preferred are those wherein:

$R_1$ is hydrogen; a straight or branched $C_1$-$C_6$ alkyl group; a $C_1$-$C_3$ alkyl group substituted with one or more substituents selected from the group consisting of methoxy, cyclopropyl, cyclobutyl, 1,3-dioxolanyl, cyano, naphthyl, $C_2$-$C_5$ alkenyloxy, and 2,3-dihydrobenzo[1,4]dioxinyl ; a $C_2$-$C_6$ alkenyl group; a $C_2$-$C_6$ alkynyl group; or a benzyl group, optionally substituted with one or more substituents selected from the group consisting of halogen, methyl, methoxy, cyano, methoxycarbonyl, and trifluoromethyl, $R_2$ is a methyl group, $R_3$ is hydrogen; a methyl group; a hydroxymethyl group; a cyanomethyl group, and $R_4$ is 1,2,3,4-tetrahydroisoquinolinyl; 1-methyl-6-fluoro-1,2,3,4-tetrahydroisoquinolinyl; a benzyloxy group optionally one or more substituted with halogen, or methyl ; or an benzylamino group optionally substituted with one or more halogen.

More preferred compounds of the formula (I) or its pharmaceutically acceptable salts of the present invention are:

7-(4-fluorobenzyloxy)-2,3-dimethyl-1H-pyrrolo[3,2-c] pyridine hydrochloride;

7-(4-fluorobenzyloxy)-2,3-dimethyl-1-(prop-2-ynyl)-1H-pyrrolo[3,2-c]pyridine hydrochloride;

1-ethyl-7-(4-fluorobenzyloxy)-2,3-dimethyl-1H-pyrrolo[3,2-c]pyridine hydrochloride;

1-cyclopropylmethyl-7-(4-fluorobenzyloxy)-2,3-dimethyl-1H-pyrrolo[3,2-c]pyridine hydrochloride;

1-allyl-7-(4-fluorobenzyloxy)-2,3-dimethyl-1H-pyrrolo[3,2-c]pyridine hydrochloride;

1-(3-fluorobenzyl)-7-(4-fluorobenzyloxy)-2,3-dimethyl-1H-pyrrolo[3,2-c]pyridine hydrochloride;

7-(4-fluorobenzyloxy)-1-(3-methoxybenzyl)-2,3-dimethyl-1H-pyrrolo[3,2-c]pyridine hydrochloride;

7-(4-fluorobenzyloxy)-2,3-dimethyl-1-(4-methylbenzyl)-1H-pyrrolo[3,2-c]pyridine hydrochloride;

1-(4-fluorobenzyl)-7-(4-fluorobenzyloxy)-2,3-dimethyl-1H-pyrrolo[3,2-c]pyridine hydrochloride;

7-(4-fluorobenzyloxy)-2,3-dimethyl-1-(4-trifluoromethylbenzyl)-1H-pyrrolo[3,2-c]pyridine hydrochloride;

7-(4-fluorobenzyloxy)-1-isobutyl-2,3-dimethyl-1H-pyrrolo[3,2-c]pyridine hydrochloride;

1-benzyl-7-(4-fluorobenzyloxy)-2,3-dimethyl-1H-pyrrolo[3,2-c]pyridine hydrochloride;

1-(2,5-dimethylbenzyl)-7-(4-fluorobenzyloxy)-2,3-dimethyl-1H-pyrrolo[3,2-c]pyridine hydrochloride;

1-(2-chlorobenzyl)-7-(4-fluorobenzyloxy)-2,3-dimethyl-1H-pyrrolo[3,2-c]pyridine hydrochloride;

1-(2-fluorobenzyl)-7-(4-fluorobenzyloxy)-2,3-dimethyl-1H-pyrrolo[3,2-c]pyridine hydrochloride;

7-(4-fluorobenzyloxy)-2,3-dimethyl-1-propyl-1H-pyrrolo[3,2-c]pyridine hydrochloride;

7-(4-fluorobenzyloxy)-1-(2-methoxyethyl)-2,3-dimethyl-1H-pyrrolo[3,2-c]pyridine hydrochloride;

7-(4-chlorobenzyloxy)-2,3-dimethyl-1H-pyrrolo[3,2-c]pyridine hydrochloride;

1-benzyl-7-(4-chlorobenzyloxy)-2,3-dimethyl-1H-pyrrolo[3,2-c]pyridine hydrochloride;

7-(2,4-dichlorobenzyloxy)-2,3-dimethyl-1H-pyrrolo[3,2-c]pyridine hydrochloride;

7-benzyloxy-2,3-dimethyl-1H-pyrrolo[3,2-c]pyridine hydrochloride;

7-(2-methylbenzyloxy)-2,3-dimethyl-1H-pyrrolo[3,2-c]pyridine hydrochloride;

7-(4-fluorobenzylamino)-2,3-dimethyl-1H-pyrrolo[3,2-c]pyridine hydrochloride;

1-benzyl-7-(4-fluorobenzylamino)-2,3-dimethyl-1H-pyrrolo[3,2-c]pyridine hydrochloride;

7-benzylamino-2,3-dimethyl-1H-pyrrolo[3,2-c]pyridine hydrochloride;

2-(2,3-dimethyl-1H-pyrrolo[3,2-c]pyridin-7-yl)-6-fluoro-1-methyl-1,2,3,4-tetrahydroisoquinoline hydrochloride;

2-(2,3-dimethyl-1H-pyrrolo[3,2-c]pyridin-7-yl)-1,2,3,4-tetrahydroisoquinoline hydrochloride;

2-[1-(4-fluorobenzyl)-2,3-dimethyl-1H-pyrrolo[3,2-c]pyridin-7-yl]-1,2,3,4-tetrahydroisoquinoline hydrochloride;

1-(4-methoxycarbonylbenzyl)-7-(1,2,3,4-tetrahydroisoquinolin-2-yl)-2,3-dimethyl-1H-pyrrolo[3,2-c]pyridine hydrochloride;

2-[1-(2,3-dihydrobenzo[1,4]dioxin-6-ylmethyl)-2,3-dimethyl-1H-pyrrolo[3,2-c]pyridin-7-yl]-1,2,3,4-tetrahydroisoquinoline hydrochloride;

1-(2-methoxyethyl)-7-(1,2,3,4-tetrahydroisoquinolin-2-yl)-2,3-dimethyl-1H-pyrrolo[3,2-c]pyridine hydrochloride;

1-(2-naphthylmethyl)-7-(1,2,3,4-tetrahydroisoquinolin-2-yl)-2,3-dimethyl-1H-pyrrolo[3,2-c]pyridine hydrochloride;

1-(2-vinyloxyethyl)-7-(1,2,3,4-tetrahydroisoquinolin-2-yl)-2,3-dimethyl-1H-pyrrolo[3,2-c]pyridine hydrochloride;

1-(1,3-dioxolan-2-ylmethyl)-7-(1,2,3,4-tetrahydroisoquinolin-2-yl)-2,3-dimethyl-1H-pyrrolo[3,2-c]pyridine hydrochloride;

1-benzyl-7-(1,2,3,4-tetrahydroisoquinolin-2-yl)-2,3-dimethyl-1H-pyrrolo[3,2-c]pyridine hydrochloride;

1-isobutyl-7-(1,2,3,4-tetrahydroisoquinolin-2-yl)-2,3-dimethyl-1H-pyrrolo[3,2-c]pyridine hydrochloride;

1-cyclobutylmethyl-7-(1,2,3,4-tetrahydroisoquinolin-2-yl)-2,3-dimethyl-1H-pyrrolo[3,2-c]pyridine hydrochloride;

2-(2,3-dimethyl-1-propyl-1H-pyrrolo[3,2-c]pyridin-7-yl)-1,2,3,4-tetrahydroisoquinoline hydrochloride;

2-(1-cyclopropylmethyl-2,3-dimethyl-1H-pyrrolo[3,2-c]pyridin-7-yl)-1,2,3,4-tetrahydroisoquinoline hydrochloride;

2-(1-ethyl-2,3-dimethyl-1H-pyrrolo[3,2-c]pyridin-7-yl)-1,2,3,4-tetrahydroisoquinoline hydrochloride;

3-[7-(3,4-dihydro-1H-isoquinolin-2-yl)-2,3-dimethylpyrrolo[3,2-c]pyridin-1-ylmethyl]-benzonitrile hydrochloride;

[7-(3,4-dihydro-1H-isoquinolin-2-yl)-2,3-dimethylpyrrolo[3,2-c]pyridin-1-yl]-acetonitrile hydrochloride;

1-benzyl-7-(1,2,3,4-tetrahydroisoquinolin-2-yl)-3-hydroxymethyl-2-methyl-1H-pyrrolo[3,2-c]pyridine hydrochloride 2-(1-benzyl-2-methyl-1H-pyrrolo[3,2-c]pyridin-7-yl)-1,2,3,4-tetrahydroisoquinoline hydrochloride;

1-benzyl-7-(3,4-dihydro-1H-isoquinolin-2-yl)-2-methyl-1H-pyrrolo[3,2-c]pyridin-3-carbonitrile hydrochloride Among them, particularly preferred compounds of the formula (I) or its pharmaceutically acceptable salts are:

7-(4-fluorobenzyloxy)-2,3-dimethyl-1H-pyrrolo[3,2-c]pyridine hydrochloride;

7-(4-fluorobenzyloxy)-2,3-dimethyl-1-(prop-2-ynyl)-1H-pyrrolo[3,2-c]pyridine hydrochloride;

1-ethyl-7-(4-fluorobenzyloxy)-2,3-dimethyl-1H-pyrrolo[3,2-c]pyridine hydrochloride;

1-cyclopropylmethyl-7-(4-fluorobenzyloxy)-2,3-dimethyl-1H-pyrrolo[3,2-c]pyridine hydrochloride;

1-allyl-7-(4-fluorobenzyloxy)-2,3-dimethyl-1H-pyrrolo[3,2-c]pyridine hydrochloride;

1-(3-fluorobenzyl)-7-(4-fluorobenzyloxy)-2,3-dimethyl-1H-pyrrolo[3,2-c]pyridine hydrochloride;

7-(4-fluorobenzyloxy)-1-(3-methoxybenzyl)-2,3-dimethyl-1H-pyrrolo[3,2-c]pyridine hydrochloride;

7-(4-fluorobenzyloxy)-2,3-dimethyl-1-(4-methylbenzyl)-1H-pyrrolo[3,2-c]pyridine hydrochloride;

1-(4-fluorobenzyl)-7-(4-fluorobenzyloxy)-2,3-dimethyl-1H-pyrrolo[3,2-c]pyridine hydrochloride;

7-(4-fluorobenzyloxy)-2,3-dimethyl-1-(4-trifluoromethylbenzyl)-1H-pyrrolo[3,2-c]pyridine hydrochloride;

7-(4-fluorobenzyloxy)-1-isobutyl-2,3-dimethyl-1H-pyrrolo[3,2-c]pyridine hydrochloride;

1-benzyl-7-(4-fluorobenzyloxy)-2,3-dimethyl-1H-pyrrolo[3,2-c]pyridine hydrochloride;

1-(2,5-dimethylbenzyl)-7-(4-fluorobenzyloxy)-2,3-dimethyl-1H-pyrrolo[3,2-c]pyridine hydrochloride;

1-(2-chlorobenzyl)-7-(4-fluorobenzyloxy)-2,3-dimethyl-1H-pyrrolo[3,2-c]pyridine hydrochloride;

1-(2-fluorobenzyl)-7-(4-fluorobenzyloxy)-2,3-dimethyl-1H-pyrrolo[3,2-c]pyridin hydrochloride;

7-(4-fluorobenzyloxy)-2,3-dimethyl-1-propyl-1H-pyrrolo[3,2-c]pyridine hydrochloride;

7-(4-fluorobenzyloxy)-1-(2-methoxyethyl)-2,3-dimethyl-1H-pyrrolo[3,2-c]pyridine hydrochloride;

2-(2,3-dimethyl-1H-pyrrolo[3,2-c]pyridin-7-yl)-1,2,3,4-tetrahydroisoquinoline hydrochloride;

2-[1-(4-fluorobenzyl)-2,3-dimethyl-1H-pyrrolo[3,2-c]pyridin-7-yl]-1,2,3,4-tetrahydroisoquinoline hydrochloride;

1-(4-methoxycarbonylbenzyl)-7-(1,2,3,4-tetrahydroisoquinolin-2-yl)-2,3-dimethyl-1H-pyrrolo[3,2-c]pyridine hydrochloride;

2-[1-(2,3-dihydrobenzo[1,4]dioxin-6-ylmethyl)-2,3-dimethyl-1H-pyrrolo[3,2-c]pyridin-7-yl]-1,2,3,4-tetrahydroisoquinoline hydrochloride;

1-(2-methoxyethyl)-7-(1,2,3,4-tetrahydroisoquinolin-2-yl)-2,3-dimethyl-1H-pyrrolo[3,2-c]pyridine hydrochloride;

1-(2-naphthylmethyl)-7-(1,2,3,4-tetrahydroisoquinolin-2-yl)-2,3-dimethyl-1H-pyrrolo[3,2-c]pyridine hydrochloride;

1-(2-vinyloxyethyl)-7-(1,2,3,4-tetrahydroisoquinolin-2-yl)-2,3-dimethyl-1H-pyrrolo[3,2-c]pyridine hydrochloride;

1-(1,3-dioxolan-2-ylmethyl)-7-(1,2,3,4-tetrahydroisoquinolin-2-yl)-2,3-dimethyl-1H-pyrrolo[3,2-c]pyridine hydrochloride;

1-benzyl-7-(1,2,3,4-tetrahydroisoquinolin-2-yl)-2,3-dimethyl-1H-pyrrolo[3,2-c]pyridine hydrochloride;

1-isobutyl-7-(1,2,3,4-tetrahydroisoquinolin-2-yl)-2,3-dimethyl-1H-pyrrolo[3,2-c]pyridine hydrochloride;

1-cyclobutylmethyl-7-(1,2,3,4-tetrahydroisoquinolin-2-yl)-2,3-dimethyl-1H-pyrrolo[3,2-c]pyridine hydrochloride;

2-(2,3-dimethyl-1-propyl-1H-pyrrolo[3,2-c]pyridin-7-yl)-1,2,3,4-tetrahydroisoquinoline hydrochloride;

2-(1-cyclopropylmethyl-2,3-dimethyl-1H-pyrrolo[3,2-c]pyridin-7-yl)-1,2,3,4-tetrahydroisoquinoline hydrochloride;

2-(1-ethyl-2,3-dimethyl-1H-pyrrolo[3,2-c]pyridin-7-yl)-1,2,3,4-tetrahydroisoquinoline hydrochloride;

3-[7-(3,4-dihydro-1H-isoquinolin-2-yl)-2,3-dimethylpyrrolo[3,2-c]pyridin-1-ylmethyl]-benzonitrile hydrochloride.

The compounds of the present invention may be pharmaceutically acceptable non-toxic salt forms. The non-toxic salts may include conventional acid addition salts used in the field of anti-ulcer agents, e.g., salts originated from inorganic acid such as hydrochloric acid, hydrobromic acid, sulfuric acid, sulfamic acid, phosphoric acid, or nitric acid, and organic acid such as acetic acid, propionic acid, succinic acid, glycolic acid, stearic acid, citric acid, maleic acid, malonic acid, methanesulfonic acid, tartaric acid, malic acid, phenylacetic acid, glutamic acid, benzoic acid, salicylic acid, 2-acetoxybenzoic acid, fumaric acid, toluenesulfonic acid, oxalic acid, or trifluoroacetic acid. Such acid addition salts may be prepared in accordance with any of the conventional methods.

The present invention includes, within its scope, a process for preparing a compound of formula (I) or a pharmaceutically acceptable salt thereof, in accordance with the following Scheme 1:

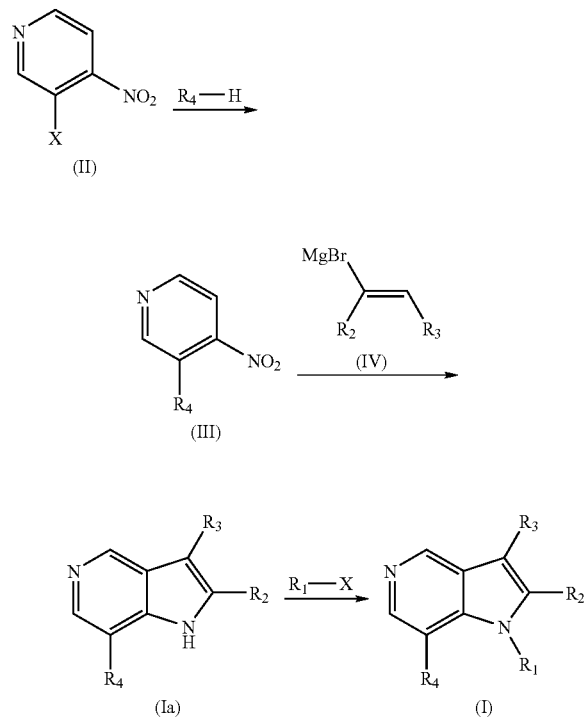

wherein, $R_1$, $R_2$, $R_3$, and $R_4$ are the same as defined in the above and X is halogen.

Specifically, the compound of formula (I) or its pharmaceutically acceptable salt may be prepared using a process which comprises: reacting a compound of formula (II) with $R_4$—H to obtain a compound of formula (III), reacting a compound of formula (III) with a compound of formula (IV) to obtain a compound of formula (Ia), and reacting the compound of formula (Ia) with $R_1$—X to obtain a compound of formula (I).

In the processes of Scheme 1, the compounds of formula (II) and (IV) are commercially available. The reaction of the compound of formula (II) and $R_4$—H may be performed in the presence of a base, such as sodium hydride, potassium tert-butoxide, sodium carbonate, or potassium hydroxide. Further, the reaction may be carried out in an organic solvent, such as anhydrous tetrahydrofuran and N,N-dimethylformamide, and at room temperature or under heating, e.g., at a temperature of 40° C.~140° C.

The cyclization reaction of a compound of formula (III) and a compound of formula (IV) may be performed in an organic solvent, e.g., anhydrous tetrahydrofuran.

Further, the reaction may be carried out at a temperature of −78° C.~−20° C. or at room temperature.

The compound of formula (Ia) is reacted with $R_1$—X to obtain a compound of formula (I). The reaction of the compound of formula (Ia) and $R_1$—X may be performed in the presence of a base, such as sodium hydride or potassium tert-butoxide. Further, the reaction may be carried out in an organic solvent, such as tetrahydrofuran or N,N-dimethylformamide, and at room temperature or at a temperature of 40° C.~100° C. In order to increase a reaction rate and/or a yield of the reaction, a catalytic amount of 18-crown-6 may be used.

In accordance with another aspect of the present invention, the compound of formula (Ic) or its pharmaceutically acceptable salt may be prepared in accordance with the following Scheme 2:

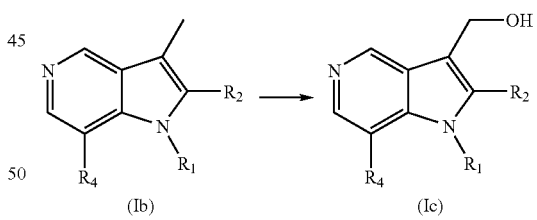

wherein, $R_1$, $R_2$ and $R_4$ are the same as defined in the above.

Specifically, the compound of formula (Ic) or its pharmaceutically acceptable salt may be prepared using a process which comprises: hydrolyzing a compound of formula (Ib), in the presence of a mmonium cerium (IV) nitrate and acetic acid.

In accordance with another aspect of the present invention, the compound of formula (Ie) or its pharmaceutically acceptable salt may be prepared using a process which comprises: performing a Mannich reaction of a compound of formula (Id), followed by reacting the resulting product with sodium cyanide or potassium cyanide, to obtain a compound of formula (Ie), as the following Scheme 3:

Scheme 3.

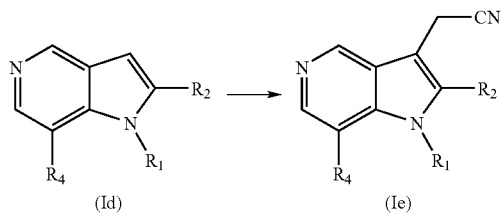

(Id)    (Ie)

wherein, $R_1$, $R_2$, and $R_4$ are the same as defined in the above.

The present invention further includes, within its scope, a pharmaceutical composition comprising a therapeutically effective amount of any of the compound of formula (I), as defined above, or a pharmaceutically acceptable salt thereof and a pharmaceutically acceptable carrier. The compound of formula (I) or a pharmaceutically acceptable salt thereof may be used for prevention and treatment of gastrointestinal inflammatory diseases and gastric acid-related diseases in mammals including human, such as gastritis, gastric ulcer, duodenal ulcer, reflux esophagitis and Zollinger-Ellison syndrome. Furthermore, the compounds or their salts of the present invention may be used for treatment of other gastrointestinal disorders where gastric antisecretory effect is desirable, e.g. in patients with gastrinomas, and in patients with acute upper gastrointestinal bleeding. The compounds or their salts of the present invention may also be used in patients in intensive care situations, and pre-and postoperatively to prevent acid aspiration and stress ulceration.

The composition of the present invention may include additives such as lactose or corn starch, lubricants such as magnesium stearate, emulsifiers, suspending agents, stabilizers, and isotonic agents. If necessary, sweetening agents and/or flavoring agents may be added.

The composition of the present invention may be administered orally or parenterally, including intravenous, intraperitoneal, subcutaneous, rectal and topical routes of administration. Therefore, the composition of the present invention may be formulated into various forms such as tablets, capsules, aqueous solutions or suspensions. In the case of tablets for oral use, carriers such as lactose, corn starch, and lubricating agents, e.g. magnesium stearate, are commonly added. In the case of capsules for oral administration, lactose and/or dried corn starch can be used as a diluent. When an aqueous suspension is required for oral use, the active ingredient may be combined with emulsifying and/or suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic. The composition of the present invention may be in the form of an aqueous solution containing pharmaceutically acceptable carriers, e.g., saline, at a pH level of 7.4. The solutions may be introduced into a patient's intramuscular blood-stream by local bolus injection.

The compounds of the present invention may be administered in an effective amount ranging from about 0.1 mg/kg to about 500 mg/kg per day to a subject patient. Of course, the dosage may be changed according to the patient's age, weight, susceptibility, or symptom.

The following examples are provided for the illustration purposes only, and are not intended to limit the scope of the invention.

Preparation 1. 3-(4-fluorobenzyloxy)-4-nitropyridine

Step 1: 3-bromopyridin-N-oxide

30% Hydrogen peroxide (41 ml) was added to a solution of 3-bromopyridine (32 g, 0.202 mol) in acetic acid (120 ml). The reaction mixture was stirred at 70° C.~80° C. for 9 hours, concentrated under reduced pressure, alkalized with excess sodium carbonate, and then diluted with methylene chloride (100 ml). The reaction mixture was filtered to discard undissolved inorganic materials. The resulting organic layer was dried on anhydrous magnesium sulfate and then concentrated under reduced pressure. The resulting residue was used in the subsequent step without further purification.

Step 2: 3-bromo-4-nitropyridin-N-oxide

Concentrated nitric acid (128 ml) and concentrated sulfuric acid (77 ml) were slowly added to a solution of 3-bromopyridin-N-oxide (31.9 g, 181.0 mmol) prepared in Step 1 in concentrated sulfuric acid (77 ml), while maintaining the temperature at 0° C.~5° C. The reaction mixture was stirred at 90° C. for 2 hours and then cooled to room temperature. The reaction mixture was added to 1000 ml of ice water, which was then brought to pH 8 with 50% sodium hydroxide solution. The resulting precipitate was filtered and dried to give the titled compound as a yellow solid (29.3 g, 72.0%).

TLC; n-hexane/ethyl acetate =1/1 (v/v); Rf=0.3

$^1$H-NMR (CDCl$_3$) δ 8.6(s, 1H) 8.4-7.9(m, 2H)

Step 3: 3-(4-fluorobenzyloxy)-4-nitropyridin-N-oxide

3-Bromo-4-nitropyridin-N-oxide (2.0 g, 9.05 mmol) prepared in Step 2, 4-fluorobenzyl alcohol (1.48 ml, 13.57 mmol), potassium carbonate (1.25 g, 9.05 mmol), and potassium hydroxide (2.03 g, 36.2 mmol) were added to 500 ml of anhydrous toluene. Tris[2-(2-methoxyethoxy)ethyl]amine (0.29 ml, 0.90 mmol) was added to the reaction mixture, which was then stirred for 1 hour at room temperature.

The reaction mixture was filtered and concentrated. The resulting residue was purified with silica gel column chromatography (ethyl acetate/n-hexane=1/1 (v/v)) to give the titled compound as a white solid (500 mg, 14.6%).

TLC; n-hexane/ethyl acetate=1/1 (v/v); Rf=0.2

$^1$H-NMR (CDCl$_3$) δ 8.5(s, 1H), 8.33(d, 1H), 8.20(m, 2H), 8.17(d, 1H), 8.15 (m, 2H), 5.21(s, 2H)

Step 4: 3-(4-fluorobenzyloxy)-4-nitropyridine

Phosphorus trichloride (3.65 ml, 41.80 mmol) was slowly added at 0° C. to a solution of 3-(4-fluorobenzyloxy)-4-nitropyridin-N-oxide (7.72 g, 27.87 mmol) prepared in Step 3 in 500 ml of ethyl acetate. The reaction mixture was stirred for 1 hour at room temperature and then alkalized with 2N sodium hydroxide solution. The separated organic layer was dried on anhydrous magnesium sulfate and then concentrated under reduced pressure. The resulting residue was used in the subsequent step without further purification.

Preparation 2. 2-(4-nitropyridin-3-yl)-1,2,3,4-tetrahydroisoquinoline

Step 1: 2-(4-nitro-1-oxypyridin-3-yl)-1,2,3,4-tetrahydroisoquinoline

3-Bromo-4-nitropyridin-N-oxide (1.0 g, 4.53 mmol) prepared in Step 2 of Preparation 1 was added to the mixture of tert-butanol (30 ml), potassium tert-butoxide (507 mg, 4.53 mmol), and 1,2,3,4-tetrahydroisoquinoline (0.79 ml, 6.34 mmol). The reaction mixture was stirred for 12 hours at room temperature. Water (10 ml) was added to the reaction mixture, which was then extracted with ethyl acetate (100 ml). The separated organic layer was dried on anhydrous magnesium sulfate and then concentrated under reduced pressure. The resulting residue was purified with silica gel column chromatography (ethyl acetate/n-hexane=1/1 (v/v)) to give the titled compound as a yellow solid (600 mg).

TLC; n-hexane/ethyl acetate=1/1 (v/v); Rf=0.2

$^1$H-NMR (CDCl$_3$) δ 8.13(s, 1H), 7.83(d, 1H), 7.71(d, 1H), 7.24(m, 3H), 7.09(m, 1H), 4.32(s, 2H), 3.46(t, 2H), 3.06(t, 2H)

Step 2: 2-(4-nitropyridin-3-yl)-1,2,3,4-tetrahydroisoquinoline

Phosphorus trichloride (3.81 ml, 28.9 mmol) was slowly added at 0° C. to a solution of 2-(4-nitro-1-oxypyridin-3-yl)-1,2,3,4-tetrahydroisoquinoline (8.5 g, 25.3 mmol) prepared in Step 1 in 100 ml of ethyl acetate. The reaction mixture was stirred for 1 hour at room temperature and then alkalized with 2N sodium hydroxide solution. The separated organic layer was dried on anhydrous magnesium sulfate and then concentrated under reduced pressure to give the titled compound as a yellow solid (5.26 g, 65.3%). The product was used in the subsequent step without further purification.

EXAMPLE 1

7-(4-fluorobenzyloxy)-2,3-dimethyl-1H-pyrrolo[3,2-c]pyridine hydrochloride 3-(4-Fluorobenzyloxy)-4-nitropyridine (6.6 g, 26.59 mmol) prepared in Preparation 1 was dissolved in anhydrous tetrahydrofuran (300 ml) under a nitrogen atmosphere. 1-Methyl-1-propenyl magnesium bromide (0.5M in tetrahydrofuran solution, 80 ml) was added at −78° C. to the solution, which was then stirred for 5 hours at −20° C. 20 ml of 20% ammonium chloride solution was added to the reaction mixture, which was then extracted with ethyl acetate (200 ml) twice. The separated organic layer was dried on anhydrous magnesium sulfate and concentrated under reduced pressure. The resulting residue was purified with silica gel column chromatography (ethyl acetate/methanol=10/1 (v/v)) and then concentrated to remove the solvent. The resulting residue was dissolved in 10 ml of ethyl acetate and saturated with hydrochloric acid gas. The resulting precipitate was filtered to give the titled compound as a white solid (910 mg, 13.5%).

TLC; ethyl acetate/methanol=10/1 (v/v); Rf=0.2

$^1$H-NMR (CDCl$_3$) δ 8.46(s, 1H), 8.20(s, 1H), 7.94(s, 1H), 7.43(m, 2H), 7.09(m, 2H), 5.18(s, 2H), 2.36(s, 3H), 2.25(s, 3H)

EXAMPLE 2

7-(4-fluorobenzyloxy)-2,3-dimethyl-1-(prop-2-ynyl)-1H-pyrrolo[3,2-c]pyridine hydrochloride The compound (25.0 mg, 0.072 mmol) prepared in Example 1 was treated with a saturated sodium bicarbonate solution to obtain 7-(4-fluorobenzyloxy)-2,3-dimethyl-1H-pyrrolo[3,2-c]pyridine (20.0 mg, 0.073 mmol). The 7-(4-fluorobenzyloxy)-2,3-dimethyl-1H-pyrrolo[3,2-c]pyridine (20.0 mg, 0.073 mmol), potassium tert-butoxide (11.0 mg, 0.109 mmol), and catalytic amount of 18-crown-6 were dissolved in anhydrous tetrahydrofuran (2 ml). Propargyl bromide (0.08 ml, 0.109 mmol) was added to the solution. The reaction mixture was stirred for 12 hours at room temperature and then concentrated under reduced pressure. The resulting residue was purified with silica gel column chromatography (ethyl acetate/methanol=10/1 (v/v)) and then concentrated to remove the solvent. The resulting residue was dissolved in 1 ml of ethyl acetate and saturated with hydrochloric acid gas. The resulting precipitate was filtered to give the titled compound as a white solid (8.5 mg, 40.1%).

TLC; ethyl acetate/methylene chloride/methanol (10/1/1, (v/v)); Rf=0.4

$^1$H-NMR (CDCl$_3$) δ 8.55(s, 1H), 7.94(s, 1H), 7.49(d, 2H), 7.14(d, 2H), 5.30(s, 2H), 5.21(s, 2H), 2.50(s, 3H), 2.42(s, 1H), 2.32(s, 3H)

EXAMPLES 3 TO 17

The titled compounds of Examples 3 to 17 were prepared, in accordance with the same procedures as in Example 2, using 7-(4-fluorobenzyloxy)-2,3-dimethyl-1H-pyrrolo[3,2-c]pyridine obtained by treating the compound of Example 1 with a saturated sodium bicarbonate solution; and, iodoethane, (bromomethyl)cyclopropane, allyl bromide, 3-fluorobenzyl chloride, 3-methoxybenzyl chloride, 4-methylbenzyl chloride, 4-fluorobenzyl bromide, 4-(trifluoromethyl) benzyl bromide, 1-iodo-2-methylpropane, benzyl bromide, 2,5-dimethylbenzyl chloride, 2-chlorobenzyl chloride, 2-fluorobenzyl chloride, 1-iodopropane, or 2-bromoethyl methyl ether.

EXAMPLE 3

1-ethyl-7-(4-fluorobenzyloxy)-2,3-dimethyl-1H-pyrrolo[3,2-c]pyridine hydrochloride $^1$H-NMR (CDCl$_3$) δ 8.55(d, 1H), 7.90(d, 1H), 7.44(t, 2H), 7.14(t, 2H), 5.21(s, 2H), 4.40(m, 2H), 2.41(s, 3H), 2.30(s, 3H), 1.32(t, 3H); (Yield: 56.5%)

EXAMPLE 4

1-cyclopropylmethyl-7-(4-fluorobenzyloxy)-2,3-dimethyl-1H-pyrrolo[3,2-c]pyridine hydrochloride $^1$H-NMR (CDCl$_3$) δ 8.55(s, 1H), 7.95(s, 1H), 7.46(d, 2H), 7.17(d, 2H), 5.28(s, 2H), 4.29(d, 2H), 2.44(s, 3H), 2.32(s, 3H), 1.21(m, 1H), 0.48(d, 2H), 0.22(d, 2H); (Yield: 58.4%)

EXAMPLE 5

1-allyl-7-(4-fluorobenzyloxy)-2,3-dimethyl-1H-pyrrolo[3,2-c]pyridine hydrochloride $^1$H-NMR (CDCl$_3$) δ 8.89(s, 1H), 8.51(s, 1H), 7.55(m, 2H), 7.08(m, 2H), 5.89(m, 1H), 5.60(s, 2H), 5.56(s, 2H), 5.49(d, 1H), 5.18(d, 1H), 2.37(s, 3H), 2.35(s, 3H); (Yield: 69.7%)

EXAMPLE 6

1-(3-fluorobenzyl)-7-(4-fluorobenzyloxy)-2,3-dimethyl-1H-pyrrolo[3,2-c]pyridine hydrochloride $^1$H-NMR (CDCl$_3$) δ 8.62(s, 1H), 8.01(m, 2H), 7.61(m, 2H), 6.79(m, 4H), 6.49(m, 1H), 5.62(s, 2H), 5.01(s, 2H), 2.25(s, 6H); (Yield: 85.4%)

EXAMPLE 7

7-(4-fluorobenzyloxy)-1-(3-methoxybenzyl)-2,3-dimethyl-1H-pyrrolo[3,2-c]pyridine hydrochloride $^1$H-NMR (CDCl$_3$) δ 8.60(s, 1H), 7.89(m, 1H), 7.48(m, 1H), 6.96(m, 5H), 6.27(s, 2H), 5.62(s, 2H), 5.11(s, 2H), 3.73(s, 3H), 2.34(s, 6H); (Yield: 45.8%)

EXAMPLE 8

7-(4-fluorobenzyloxy)-2,3-dimethyl-1-(4-methylbenzyl)-1H-pyrrolo[3,2-c]pyridine hydrochloride $^1$H-NMR (CDCl$_3$) δ 8.61(s, 1H), 7.51(s, 1H), 7.10(s, 4H), 6.98(s, 2H), 6.65(s, 2H); 5.62(s, 2H), 5.30(s, 2H), 2.34(s, 6H); (Yield: 35.7%)

EXAMPLE 9

1-(4-fluorobenzyl)-7-(4-fluorobenzyloxy)-2,3-dimethyl-1H-pyrrolo[3,2-c]pyridine hydrochloride $^1$H-NMR (CDCl$_3$) δ 8.60(d, 1H), 7.91(s, 1H), 7.10(m, 2H), 7.00(m, 4H), 6.71(m, 2H), 5.60(s, 2H), 5.09(s, 2H), 2.34(s, 3H), 2.33(s, 3H); (Yield: 66.2%)

EXAMPLE 10

7-(4-fluorobenzyloxy)-2,3-dimethyl-1-(4-trifluoromethylbenzyl)-1H-pyrrolo[3,2-c]pyridine hydrochloride $^1$H-NMR (CDCl$_3$) δ 8.63(d, 1H), 7.92(d, 1H), 7.55(d, 2H), 7.02(m, 4H), 6.82(d, 2H), 5.67(s, 2H), 5.06(s, 2H), 2.36(s, 3H), 2.33(s, 3H); (Yield: 33.2%)

EXAMPLE 11

7-(4-fluorobenzyloxy)-1-isobutyl-2,3-dimethyl-1H-pyrrolo[3,2-c]pyridine hydrochloride $^1$H-NMR (CDCl$_3$) δ 8.53(d, 1H), 7.91(d, 1H), 7.44(t, 2H), 7.15(t, 2H), 5.16(s, 2H); 4.11(d, 2H), 2.38(s, 3H), 2.30(s, 3H), 2.04(m, 1H), 0.72(s, 3H), 0.70(s, 3H); (Yield: 34.1%)

EXAMPLE 12

1-benzyl-7-(4-fluorobenzyloxy)-2,3-dimethyl-1H-pyrrolo[3,2-c]pyridine hydrochloride $^1$H-NMR (CDCl$_3$) δ 8.34(s, 1H), 7.52(s, 1H), 7.37(m, 2H), 7.09(m, 2H), 7.04(m, 3H), 6.97(m, 2H), 5.66(s, 2H), 5.26(s, 2H), 2.36(s, 3H), 2.34(s, 3H); (Yield: 45.8%)

EXAMPLE 13

1-(2,5-dimethylbenzyl)-7-(4-fluorobenzyloxy)-2,3-dimethyl-1H-pyrrolo[3,2-c]pyridine hydrochloride $^1$H-NMR (CDCl$_3$) δ 8.62(d, 1H), 7.85(d, 1H), 7.45(m, 1H), 7.07(m, 2H), 6.92(m, 4H), 5.46(s, 2H), 4.98(s, 2H), 2.48(s, 3H), 2.31(s, 3H), 2.12(s, 3H), 2.02(s, 3H); (Yield: 49.8%)

EXAMPLE 14

1-(2-chlorobenzyl)-7-(4-fluorobenzyloxy)-2,3-dimethyl-1H-pyrrolo[3,2-c]pyridine hydrochloride $^1$H-NMR (CDCl$_3$) δ 8.62(s, 1H), 7.89(s, 1H), 7.41(d, 2H), 7.14(t, 2H), 6.95(d, 4H), 6.07(s, 1H), 5.66(s, 2H), 5.03(s, 2H), 2.37(s, 3H), 2.31(s, 3H); (Yield: 58.9%)

EXAMPLE 15

1-(2-fluorobenzyl)-7-(4-fluorobenzyloxy)-2,3-dimethyl-1H-pyrrolo[3,2-c]pyridine hydrochloride $^1$H-NMR (CDCl$_3$) δ 8.62(s, 1H), 7.92(s, 1H), 7.31(m, 1H), 7.05(m, 6H), 6.31(s, 1H), 5.69(s, 2H), 5.10(s, 2H), 2.36(s, 3H), 2.34(s, 3H); (Yield: 49.8%)

EXAMPLE 16

7-(4-fluorobenzyloxy)-2,3-dimethyl-1-propyl-1H-pyrrolo[3,2-c]pyridine hydrochloride $^1$H-NMR (CDCl$_3$) δ 8.34(s, 1H), 8.11(s, 1H), 7.61(m, 2H), 7.17(m, 2H), 5.32(s, 2H), 4.39(s, 2H), 2.53(s, 3H), 2.33(s, 3H), 1.81(m, 2H), 0.79(d, 3H); (Yield: 61.1%)

EXAMPLE 17

7-(4-fluorobenzyloxy)-1-(2-methoxyethyl)-2,3-dimethyl-1H-pyrrolo[3,2-c]pyridine hydrochloride $^1$H-NMR (CDCl$_3$) δ 8.54(s, 1H), 7.91(s, 1H), 7.44(d, 2H), 7.15(d, 2H), 5.30(s, 2H), 5.21(t, 2H), 3.57(d, 2H), 3.21(s, 3H), 2.46(s, 3H), 2.05(s, 3H); (Yield: 54.3%)

EXAMPLE 18

7-(4-chlorobenzyloxy)-2,3-dimethyl-1H-pyrrolo[3,2-c]pyridine hydrochloride

Step 1: 3-(4-chlorobenzyloxy)-4-nitropyridine

In accordance with the same procedures as in Steps 3 and 4 of Preparation 1, except for using 3-bromo-4-nitropyridin-N-oxide prepared in Step 2 of Preparation 1 and 4-chlorobenzyl alcohol, the titled compound was obtained as a white solid. (Yield: 25.3% )

$^1$H-NMR (CDCl$_3$) δ 8.40(s, 1H), 8.31(d, 1H), 8.25(m, 2H), 8.19(d, 1H), 8.13 (m, 2H), 5.20(s, 2H)

Step 2: 7-(4-chlorobenzyloxy)-2,3-dimethyl-1H-pyrrolo[3,2-c]pyridine hydrochloride In accordance with the same procedures as in Example 1, except for using 3-(4-chlorobenzyloxy)-4-nitropyridine prepared in Step 1, the titled compound was obtained as a white solid. (Yield: 13.4% )

¹H-NMR (CDCl₃) δ 8.43(s, 1H), 8.19(s, 1H), 7.93(s, 1H), 7.44(m, 2H), 7.10(m, 2H), 5.15(s, 2H), 2.37(s, 3H), 2.24(s, 3H)

EXAMPLE 19

1-benzyl-7-(4-chlorobenzyloxy)-2,3-dimethyl-1H-pyrrolo[3,2-c]pyridine hydrochloride In accordance with the same procedures as in Example 2, except for using 7-(4-chlorobenzyloxy)-2,3-dimethyl-1H-pyrrolo[3,2-c]pyridine obtained by treating the compound of Example 18 with a saturated sodium bicarbonate solution and benzyl bromide, the titled compound was obtained as a white solid. (Yield: 38.8% )

¹H-NMR (CDCl₃) δ 8.33(s, 1H), 7.50(s, 1H), 7.35(m, 2H), 7.08(m, 2H), 7.01(m, 3H), 6.89(m, 2H), 5.63(s, 2H), 5.21(s, 2H), 2.34(s, 3H), 2.32(s, 3H)

EXAMPLE 20

7-(2,4-dichlorobenzyloxy)-2,3-dimethyl-1H-pyrrolo[3,2-c]pyridine hydrochloride

Step 1: 3-(2,4-dichlorobenzyloxy)-4-nitropyridine

In accordance with the same procedures as in Steps 3 and 4 of Preparation 1, except for using 3-bromo-4-nitropyridin-N-oxide prepared in Step 2 of Preparation 1 and 2,4-dichlorobenzyl alcohol, the titled compound was obtained (Yield: 68.2%).

¹H-NMR (CDCl₃) δ 8.40(s, 1H), 8.38(s, 1H), 8.31(d, 1H), 8.25(m, 1H), 8.22(m, 1H), 8.19(d, 1H), 5.20(s, 2H)

Step 2: 7-(2,4-dichlorobenzyloxy)-2,3-dimethyl-1H-pyrrolo[3,2-c]pyridine hydrochloride In accordance with the same procedures as in Example 1, except for using 3-(2,4-dichlorobenzyloxy)-4-nitropyridine prepared in Step 1, the titled compound was obtained as a white solid. (Yield: 11.3% )

¹H-NMR (CDCl₃) δ 8.43(s, 1H), 8.32(s, 1H), 8.19(s, 1H), 7.93(s, 1H), 7.10(m, 2H), 5.15(s, 2H), 2.37(s, 3H), 2.24(s, 3H)

EXAMPLES 21 AND 22

The titled compounds of Examples 21 and 22 were prepared, in accordance with the same procedures as in Example 20, using 3-bromo-4-nitropyridin-N-oxide prepared in Step 2 of Preparation 1; and, benzyl alcohol, or 2-methylbenzyl alcohol.

EXAMPLE 21

7-benzyloxy-2,3-dimethyl-1H-pyrrolo[3,2-c]pyridine hydrochloride

¹H-NMR (CDCl₃) δ 8.42(s, 1H), 8.15(s, 1H), 8.00(s, 1H), 7.44(m, 3H), 7.10(m, 2H), 5.13(s, 2H), 2.35(s, 3H), 2.25(s, 3H); (Yield: 15.3%)

EXAMPLE 22

7-(2-methylbenzyloxy)-2,3-dimethyl-1H-pyrrolo[3,2-c]pyridine hydrochloride

¹H-NMR (CDCl₃) δ 8.45(s, 1H), 8.13(s, 1H), 7.98(s, 1H), 7.44(m, 4H), 5.13(s, 2H), 2.35(s, 3H), 2.25(s, 3H), 1.58(s, 3H); (Yield: 14.7%)

EXAMPLE 23

7-(4-fluorobenzylamino)-2,3-dimethyl-1H-pyrrolo[3,2-c]pyridine hydrochloride

Step 1: 3-(4-fluorobenzylamino)-4-nitropyridine

In accordance with the same procedures as in Preparation 2, except for using 3-bromo-4-nitropyridin-N-oxide prepared in Step 2 of Preparation 1 and 4-fluorobenzylamine, the titled compound was obtained as a yellow solid. (Yield: 35.8%)

¹H-NMR (CDCl₃) δ 8.43(s, 1H), 8.29(d, 1H), 8.21(m, 2H), 8.11(d, 1H), 8.19 (m, 2H), 5.84(d, 2H)

Step 2: (4-fluorobenzyl)-(4-nitropyridin-3-yl)-carbamic acid tert-butyl ester Di-tert-butyl dicarbonate(4.06 g, 18.62 mmol) and N,N-dimethylaminopyridine (1.14 g, 9.31 mmol) were added to a solution of 3-(4-fluorobenzylamino)-4-nitropyridine (1.53 g, 6.21 mmol) prepared in Step 1 in 60 ml of tetrahydrofuran. The reaction mixture was stirred for 24 hours and then concentrated under reduced pressure. The resulting residue was purified with silica gel column chromatography (ethyl acetate/n-hexane=1/1 (v/v)) to give the titled compound as yellow oil (1.5 g, 75.8%).

¹H-NMR (CDCl₃) δ 8.61(s, 1H), 7.31(m, 3H), 7.17(m, 2H), 6.72(d, 1H), 5.11(s, 2H), 1.2(s, 9H)

Step 3: 7-(4-fluorobenzylamino)-2,3-dimethyl-1H-pyrrolo[3,2-c]pyridine hydrochloride (4-Fluorobenzyl)-(4-nitropyridin-3-yl)-carbamic acid tert-butyl ester (5.1 g) prepared in Step 2 was dissolved in anhydrous tetrahydrofuran (100 ml) under a nitrogen atmosphere. 1-Methyl-1-propenyl magnesium bromide (0.5M in tetrahydrofuran solution, 55.0 ml, 65.2 mmol) was added at −78° C. to the solution, which was then stirred for 5 hours at −20° C. 20 ml of 20% ammonium chloride solution was added to the reaction mixture, which was then extracted with ethyl acetate (200 ml) twice. The separated organic layer was dried on anhydrous magnesium sulfate and concentrated under reduced pressure. The resulting residue was purified with silica gel column chromatography (ethyl acetate/methanol=10/1 (v/v)), dissolved in 1 ml of ethyl acetate and then saturated with hydrochloric acid gas. The resulting precipitate was filtered to give the titled compound as a pale yellow solid (2.1 g, 35.0%).

¹H-NMR (CDCl₃) δ 8.41(brs, 1H), 8.13(s, 1H), 7.48(s, 1H), 7.15(d, 2H), 7.01(d, 2H), 5.14(s, 2H), 2.51(s, 3H), 2.48 (s, 3H)

EXAMPLE 24

1-benzyl-7-(4-fluorobenzylamino)-2,3-dimethyl-1H-pyrrolo[3,2-c]pyridine hydrochloride In accordance with the same procedures as in Example 2, except for using 7-(4-fluorobenzylamino)-2,3-dimethyl-1H-pyrrolo[3,2-c]pyridine obtained by treating the compound of Example 23 with a saturated sodium bicarbonate solution and benzyl bromide, the titled compound was obtained as a white solid. (Yield: 15.8%)
$^1$H-NMR (CDCl$_3$) δ 8.31(s, 1H), 7.52(s, 1H), 7.28(m, 2H), 7.07(m, 2H), 7.00(m, 3H), 6.87(m, 2H), 5.60(s, 2H), 5.20(s, 2H), 2.33(s, 3H), 2.30(s, 3H)

EXAMPLE 25

7-benzylamino-2,3-dimethyl-1H-pyrrolo[3,2-c]pyridine hydrochloride

In accordance with the same procedures as in Example 23, except for using 3-bromo-4-nitropyridin-N-oxide prepared in Step 2 of Preparation 1 and benzylamine, the titled compound was obtained as a white solid. (Yield: 11.3%)
$^1$H-NMR (CDCl$_3$) δ 8.43(brs, 1H), 8.12(s, 1H), 7.85(s, 1H), 7.13(m, 3H), 7.02(m 2H), 5.56(s, 2H), 2.53(s, 3H), 2.47(s, 3H)

EXAMPLE 26

2-(2,3-dimethyl-1H-pyrrolo[3,2-c]pyridin-7-yl)-6-fluoro-1-methyl-1,2,3,4-tetrahydroisoquinoline hydrochloride Step 1: 6-fluoro-1-methyl-2-(4-nitropyridin-3-yl)-1,2,3,4-tetrahydroisoquinoline In accordance with the same procedures as in Preparation 2, except for using 6-fluoro-1-methyl-1,2,3,4-tetrahydroisoquinoline prepared according to the methods disclosed in WO 94/14,795, the titled compound was obtained as a pale yellow solid. (Yield: 59.8%) The product was used in the subsequent step without further purification.

Step 2: 2-(2,3-dimethyl-1H-pyrrolo[3,2-c]pyridin-7-yl)-6-fluoro-1-methyl-1,2,3,4-tetrahydroisoquinoline hydrochloride In accordance with the same procedures as in Example 1, except for using 6-fluoro-1-methyl-2-(4-nitropyridin-3-yl)-1,2,3,4-tetrahydroisoquinoline prepared in Step 1, the titled compound was obtained as a white solid. (Yield: 14.8%)
$^1$H-NMR (CDCl$_3$) δ 10.21(s, 1H), 8.50(s, 1H), 7.88(s, 1H), 7.21(m, 2H), 7.07(s, 1H), 4.35(s, 2H), 3.49(t, 1H), 3.15(t, 2H), 2.38(d, 3H), 2.54(s, 3H), 2.27(s, 3H)

EXAMPLE 27

2-(2,3-dimethyl-1H-pyrrolo[3,2-c]pyridin-7-yl)-1,2,3,4-tetrahydroisoquinoline hydrochloride 2-(4-Nitropyridin-3-yl)-1,2,3,4-tetrahydroisoquinoline (2.0 g, 7.835 mmol) prepared in Preparation 2 was dissolved in anhydrous tetrahydrofuran (100 ml) under a nitrogen atmosphere. 1-Methyl-1-propenyl magnesium bromide (0.5M in tetrahydrofuran solution, 9.4 ml) was added at −78° C. to the solution, which was then stirred for 20 minutes at the same temperature. 10 ml of 20% ammonium chloride solution was added to the reaction mixture, which was then extracted with ethyl acetate (100 ml) twice. The separated organic layer was dried on anhydrous magnesium sulfate and concentrated under reduced pressure. The resulting residue was purified with silica gel column chromatography (methylene chloride/methanol=10/1 (v/v)), dissolved in 5 ml of ethyl acetate and then saturated with hydrochloric acid gas. The resulting precipitate was filtered to give the titled compound as a white solid (850 mg, 19.5%).
$^1$H-NMR (CDCl$_3$) δ 10.21(s, 1H), 8.50(s, 1H), 7.88(s, 1H), 7.21(m, 3H), 7.07(d, 1H), 4.35(s, 2H), 3.49(t, 2H), 3.15(t, 2H), 2.54(s, 3H), 2.27(s, 3H)

EXAMPLES 28 TO 42

The titled compounds of Examples 28 to 42 were prepared, in accordance with the same procedures as in Example 2, using 2-(2,3-dimethyl-1H-pyrrolo[3,2-c]pyridin-7-yl)-1,2,3,4-tetrahydroisoquinoline obtained by treating the compound of Example 27 with a saturated sodium bicarbonate solution; and, 4-fluorobenzylchloride, methyl-4-(bromomethyl)benzoate, 6-chloromethyl-2,3-dihydrobenzo[1,4]dioxin, 2-bromoethyl methyl ether, 2-bromomethylnaphthalene, 2-chloroethyl vinyl ether, 2-bromomethyl-1,3-dioxolane, benzyl bromide, 1-iodo-2-methylpropane, (bromomethyl)cyclobutane, 1-iodopropane, (bromomethyl)cyclopropane, iodoethane, 3-bromomethylbenzonitrile, or bromoacetonitrile.

EXAMPLE 28

2-[1-(4-fluorobenzyl)-2,3-dimethyl-1H-pyrrolo[3,2-c]pyridin-7-yl]-1,2,3,4-tetrahydroisoquinoline hydrochloride $^1$H-NMR (CDCl$_3$) δ 8.50(s, 1H), 7.88(s, 1H), 7.21(m, 3H), 7.10(m, 2H), 7.07(d, 1H), 6.98(m, 2H), 5.65(s, 2H), 4.35(s, 2H), 3.49(t, 2H), 3.15(t, 2H), 2.54(s, 3H), 2.27(s, 3H); (Yield: 25.8%)

EXAMPLE 29

1-(4-methoxycarbonylbenzyl)-7-(1,2,3,4-tetrahydroisoquinolin-2-yl)-2,3-dimethyl-1H-pyrrolo[3,2-c]pyridine hydrochloride $^1$H-NMR (CDCl$_3$) δ 8.74(s, 1H), 8.16(s, 1H), 7.91(m, 2H), 7.22(m, 2H), 7.19(m, 2H), 6.74(m, 2H), 5.91(m, 2H), 4.04(s, 2H), 3.96(s, 3H), 3.31(m, 2H), 2.79(m, 2H), 2.38(s, 3H), 2.29(s, H); (Yield: 38.8%)

EXAMPLE 30

2-[1-(2,3-dihydrobenzo[1,4]dioxin-6-ylmethyl)-2,3-dimethyl-1H-pyrrolo[3,2-c]pyridin-7-yl]-1,2,3,4-tetrahydroisoquinoline hydrochloride $^1$H-NMR (CDCl$_3$) δ 8.36(s, 1H), 7.58(m, 4H), 7.15(s, 1H), 7.10(m, 3H), 5.16(s, 2H), 4.69(s, 2H), 4.33(m, 2H), 3.57(m, 2H), 3.01(m, 2H), 2.57(s, 3H), 2.47(s, 3H); (Yield: 35.3%)

EXAMPLE 31

1-(2-methoxyethyl)-7-(1,2,3,4-tetrahydroisoquinolin-2-yl)-2,3-dimethyl-1H-pyrrolo[3,2-c]pyridine hydrochloride $^1$H-NMR (CDCl$_3$) δ 8.69(s, 1H), 8.14(s, 1H), 7.22(m, 3H), 7.06(m, 1H), 4.64(m, 2H), 4.19(m, 2H), 3.50(m, 2H), 3.34(m, 2H), 3.23(m, 2H), 3.13(s, 3H), 2.49(s, 3H). 2.36(s, 3H); (Yield: 58.9%)

EXAMPLE 32

1-(2-naphthylmethyl)-7-(1,2,3,4-tetrahydroisoquinolin-2-yl)-2,3-dimethyl-1H-pyrrolo[3,2-c]pyridine hydrochloride $^1$H-NMR (CDCl$_3$) δ 8.35(s, 1H), 8.20(m, 1H), 7.73(m, 6H), 7.18(m, 5H), 5.89(s, 2H), 4.06(s, 2H), 3.27(m, 2H), 2.87(m, 2H), 2.38(s, 3H), 2.32(s, 3H); (Yield: 63.2%)

EXAMPLE 33

1-(2-vinyloxyethyl)-7-(1,2,3,4-tetrahydroisoquinolin-2-yl)-2,3-dimethyl-1H-pyrrolo[3,2-c]pyridine hydrochloride $^1$H-NMR (CDCl$_3$) δ 8.63(s, 1H), 8.13(s, 1H), 7.25(m, 3H), 7.12(m, 1H), 4.58(m, 2H), 4.20(m, 2H), 3.81(m, 2H), 3.52(m, 3H), 3.39(m, 1H), 3.18(m, 1H), 2.96(m, 1H), 2.49(s, 3H), 2.34(s, 3H); (Yield: 66.3%)

EXAMPLE 34

1-(1,3-dioxolan-2-ylmethyl)-7-(1,2,3,4-tetrahydroisoquinolin-2-yl)-2,3-dimethyl-1H-pyrrolo[3,2-c]pyridine hydrochloride $^1$H-NMR (CDCl$_3$) δ 8.35(s, 1H), 8.10(s, 1H), 7.85(m, 2H), 7.23(m, 3H), 5.91(d, 2H), 4.35(s, 2H), 4.04(m, 4H), 3.96(s, 2H), 2.79(m, 2H), 2.38(s, 3H), 2.29(s, H); (Yield: 55.8%).

EXAMPLE 35

1-benzyl-7-(1,2,3,4-tetrahydroisoquinolin-2-yl)-2,3-dimethyl-1H-pyrrolo[3,2-c]pyridine hydrochloride $^1$H-NMR (CDCl$_3$) δ 8.76(s, 1H), 8.14(s, 1H), 7.11(m, 4H), 6.74(m, 4H), 5.83(m, 2H), 4.16(m, 2H), 3.26(m, 2H), 2.90(m, 2H), 2.46(s, 3H), 2.38(s, 3H); (Yield: 59.1%)

EXAMPLE 36

1-isobutyl-7-(1,2,3,4-tetrahydroisoquinolin-2-yl)-2,3-dimethyl-1H-pyrrolo[3,2-c]pyridine hydrochloride $^1$H-NMR (CDCl$_3$) δ 8.75(s, 1H), 8.17(s, 1H), 7.33(m, 2H), 7.08(m, 2H), 4.25(m, 4H), 3.47(m, 2H), 3.25(m, 2H), 2.54(s, 3H), 2.37(s, 3H), 1.97(m, 1H), 1.60(d, 6H); (Yield: 65.3%)

EXAMPLE 37

1-cyclobutylmethyl-7-(1,2,3,4-tetrahydroisoquinolin-2-yl)-2,3-dimethyl-1H-pyrrolo[3,2-c]pyridine hydrochloride $^1$H-NMR (CDCl$_3$) δ 8.70(s, 1H), 8.03(s, 1H), 7.23(m, 2H), 7.08(m, 2H), 4.52(d, 2H), 4.30(m, 2H), 3.43(m, 2H), 3.10(m, 2H), 2.43(s, 3H), 2.33(s, 3H), 1.74(m, 4H), 1.67(m, 1H), 1.57(m, 2H); (Yield: 55.4%)

EXAMPLE 38

2-(2,3-dimethyl-1-propyl-1H-pyrrolo[3,2-c]pyridin-7-yl)-1,2,3,4-tetrahydroisoquinoline hydrochloride $^1$H-NMR (CDCl$_3$) δ 8.66(s, 1H), 8.15(s, 1H), 7.22(m, 3H), 7.08(m, 1H), 4.37(m, 4H), 3.49(m, 2H), 3.30(m, 1H), 3.01(m, 1H), 2.48(s, 3H), 2.34(s, 3H), 1.56(m, 2H), 0.68(t, 3H); (Yield: 59.9%)

EXAMPLE 39

2-(1-cyclopropylmethyl-2,3-dimethyl-1H-pyrrolo[3,2-c]pyridin-7-yl)-1,2,3,4-tetrahydroisoquinoline $^1$H-NMR (CDCl$_3$) δ 8.15(s, 1H), 7.57(s, 1H), 7.32(m, 3H), 7.09(m, H), 4.43(m, 4H), 3.49(m, 4H), 2.58(s, 3H), 2.39(s, 3H), 1.21(m, 1H), 0.39(m, 2H), 0.14(m, 2H); (Yield: 65.8%)

EXAMPLE 40

2-(1-ethyl-2,3-dimethyl-1H-pyrrolo[3,2-c]pyridin-7-yl)-1,2,3,4-tetrahydroisoquinoline hydrochloride $^1$H-NMR (CDCl$_3$) δ 8.65(s, 1H), 8.13(s, 1H), 7.23(m, 3H), 7.08(m, 1H), 4.59(m, 2H), 4.23(m, 2H), 3.51(m, 2H), 3.23(m, 2H), 2.45(s, 3H), 2.34(s, 3H), 1.25(d, 3H); (Yield: 65.8%)

EXAMPLE 41

3-[7-(3,4-dihydro-1H-isoquinolin-2-yl)-2,3-dimethylpyrrolo[3,2-c]pyridin-1-ylmethyl]-benzonitrile hydrochloride $^1$H-NMR (CDCl$_3$) δ 8.36(s, 1H), 7.58(m, 4H), 7.10(s, 1H), 7.08(m, 3H), 6.98(s, 1H), 5.68(s, 2H), 4.39(s, 2H), 3.68(m, 2H), 2.98(m, 2H), 2.56(s, 3H), 2.50(s, 3H); (Yield: 55.7%)

EXAMPLE 42

[7-(3,4-dihydro-1H-isoquinolin-2-yl)-2,3-dimethylpyrrolo[3,2-c]pyridin-1-yl]-acetonitrile hydrochloride $^1$H-NMR (CDCl$_3$) δ 8.35(s, 1H), 7.58(m, 4H), 7.10(s, 1H), 4.38(s, 2H), 4.35(s, 2H), 3.61(m, 2H), 2.89(m, 2H), 2.58(s, 3H), 2.54(s, 3H); (Yield: 65.3%)

EXAMPLE 43

1-benzyl-7-(1,2,3,4-tetrahydroisoquinolin-2-yl)-3-hydroxymethyl-2-methyl-1H-pyrrolo[3,2-c]pyridine hydrochloride The compound (250.4 mg, 0.62 mmol) prepared in Example 35 was treated with a saturated sodium bicarbonate solution to obtain 1-benzyl-7-(1,2,3,4-tetrahydroisoquinolin-2-yl)-2,3-dimethyl-1H-pyrrolo[3,2-c]pyridine (216.8 mg, 0.59 mmol). A mmonium cerium (IV) nitrate (973 mg, 1.77 mmol) was added at room temperature to a solution of 1-benzyl-7-(1,2,3,4-tetrahydroisoquinolin-2-yl)-2,3-dimethyl-1H-pyrrolo[3,2-c]pyridine (216.8 mg, 0.59 mmol) in acetic acid (3 ml) and then stirred for 4 hours at 55° C. The reaction mixture was cooled to room temperature, added to water, and then extracted with ethyl acetate. The separated organic layer was washed with a saturated sodium chloride solution, dried on anhydrous magnesium sulfate, and then concentrated under reduced pressure. The resulting residue was dissolved in methanol (10 ml). 2N Lithium hydroxide (2.5 ml) was added to the reaction mixture, which was then stirred for 1 hour at room temperature. The reaction mixture was neutralized with IN hydrochloride, concentrated under reduced pressure, and then extracted with ethyl acetate. The separated organic layer was dried on anhydrous magnesium sulfate, filtered, and then concentrated under reduced pressure. The resulting residue was purified with silica gel column chromatography to give 1-benzyl-7-(1,2,3,4-tetrahydroisoquinolin-2-yl)-3-hydroxymethyl-2-methyl-1H -pyrrolo[3,2-c]pyridine, which was then dissolved in 10 ml of ethyl acetate and saturated with hydrochloric acid gas. The resulting precipitate was filtered to give the titled compound as a white solid (200 mg, 76.8%).

$^1$H-NMR (CDCl$_3$) δ 8.77(s, 1H), 8.18(s, 1H), 7.12(m, 4H), 6.75(m, 5H), 5.82(s, 2H), 4.15(m, 2H), 4.09(s, 2H), 3.25(m, 2H), 2.89(m, 2H), 2.38(s, 3H)

EXAMPLE 44

2-(1-benzyl-2-methyl-1H-pyrrolo[3,2-c]pyridin-7-yl)-1,2,3,4-tetrahydroisoquinoline hydrochloride Step 1: 2-(2-methyl-1H-pyrrolo[3,2-c]pyridin-7-yl)-1,2,3,4-tetrahydroisoquinolinehydrochloride In accordance with the same procedures as in Example 27, except for using 2-(4-nitropyridin-3-yl)-1,2,3,4-tetrahydroisoquinoline prepared in Preparation 2 and isopropenyl magnesium bromide, the titled compound was obtained as a white solid. (Yield: 18.4% ) The product was used in the subsequent step without further purification.

Step 2: 2-(1-benzyl-2-methyl-1H-pyrrolo[3,2-c]pyridin-7-yl)-1,2,3,4-tetrahydroisoquinoline hydrochloride In accordance with the same procedures as in Example 2, except for using 2-(2-methyl-1H-pyrrolo[3,2-c]pyridin-7-yl)-1,2,3,4-tetrahydroisoquinoline obtained by treating the compound of Step 1 with a saturated sodium bicarbonate solution and benzyl bromide, the titled compound was obtained as a white solid. (Yield: 25.3%)

$^1$H-NMR (CDCl$_3$) δ 8.36(s, 1H), 7.54(m, 4H), 7.24(m, 5H), 7.18(d, 1H), 7.10(d, 1H), 6.15(s, 1H), 5.24(s, 2H), 4.36 (s, 2H), 3.65(m, 2H), 2.69(m, 2H), 2.34(d, 3H)

EXAMPLE 45

1-benzyl-7-(3,4-dihydro-1H-isoquinolin-2-yl)-2-methyl-1H-pyrrolo[3,2-c]pyridin-3-carbonitrile hydrochloride Dimethylamine (1.05 ml, 2.1 mmol), acetic acid (0.81 ml), and formaldehyde (0.042 ml) were added to a solution of 2-(1-benzyl-2-methyl-1H-pyrrolo[3,2-c]pyridin-7-yl)-1,2,3,4-tetrahydroisoquinoline hydrochloride (600 mg, 1.71 mmol) prepared in Example 44 in ethanol (5 ml). The resulting mixture was refluxed under stirring overnight and concentrated under reduced pressure. The resulting residue was purified with silica gel column chromatography. The resulting compound (300 mg, 0.73 mmol) was dissolved in ethanol (2 ml). Iodomethane (0.091 ml, 0.46 mmol) was added to the solution, which was stirred overnight at room temperature. The resulting white product (100 mg, 0.18 mmol) was dissolved in N,N-dimethylformamide (3 ml). Sodium cyanide (34 mg, 0.72 mmol) was added to the solution, which was then stirred for 5 hours at 100° C. Water was added to the reaction mixture, which was then extracted with ethyl acetate. The separated organic layer was dried on anhydrous magnesium sulfate and concentrated under reduced pressure. The resulting residue was purified with silica gel column chromatography, dissolved in ether, and then saturated with hydrochloric acid gas to give the titled compound as a white solid (25 mg, 34.0%).

$^1$H-NMR (CDCl$_3$) δ 8.23(d, 1H), 7.54(m, 4H), 7.24(m, 5H), 7.18(d, 1H), 5.81(s, 2H), 5.23(s, 2H), 4.34(s, 2H), 3.66 (m, 2H), 2.70(m, 2H), 2.33(s, 3H)

TEST EXAMPLE 1

Inhibitory effects on proton pump (H$^+$/K$^+$-ATPase) activity 1-1. Preparation of gastric proton pump vesicles The hog fundic regions containing parietal and peptic cells were scraped with slide-glass. The collected cells were suspended in 10 ml of 0.25M sucrose buffer and homogenized using a tight-fitting Teflon-glass homogenizer. The homogenate was centrifuged for 35 min at 8,000 rpm and the pellet was discarded. The supernatant was further centrifuged for 75 min at 25,000 rpm. The resulting pellets were re-suspended in the sucrose buffer (10 ml), and then the suspension was laid onto discontinuous density gradients consisting of 0.25M sucrose buffer and isolation medium containing 9% Ficoll (w/w). After being centrifuged for 3 hours and 15 minutes at 100,000×g, the material at the interface of sucrose buffer and Ficoll solution was collected and then centrifuged for 40 minutes at 100,000×g. The resulting pellets were re-suspended in 1 ml of 5 mM Hepes/Tris buffer (pH 6.1). This material was lyophilized and stored at −70° C. and used as an enzyme source of the in vitro enzyme reaction assay of proton pump.

1-2. Measurement of inhibitory effects on proton pump (H$^+$/K$^+$-ATPase) activity The inhibitory effects of the compounds of the present invention against proton pump activity were evaluated in 96-well plate. In this assay, the K$^+$specific H$^+$/K$^+$-ATPase activity was calculated based on the difference between the activity of H$^+$/K$^{30}$-ATPase activity with K$^{30}$ and without K$^{30}$ ion. In 96-well plate, 1% dimethylsulfoxide (DMSO) in buffer was added to negative and positive control groups and the diluted compounds of the present invention in buffer were added to test group. All assays were performed in 100μl reaction volume at room temperature, and the hog gastric vesicle was kept in ice before use. At the beginning of the reaction, 10μl of reaction buffer containing 1% DMSO was added to the negative and positive control groups and to reaction buffer each concentration of compounds in the test group. Then lyophilized vesicle in 5mM Pipes/Tris buffer (pH 6.1) was pre-incubated in the presence of various concentrations of test compounds. After a 5 minute incubation, negative and positive buffers were respectively added to the previous reaction mixture. As the substrate, ATP was added to the reaction buffer, and incubated for 30 minutes at 37° C. Enzymatic activity was stopped by the addition of colorimetric reagent (2X malachite green, 1X ammonium molybdate, X polyvinyl alcohol, 2X $H_2O$) and the amount of mono phosphate (Pi) in the reaction was measured at 620nm using the micro plate reader (Genios Pro, TECAN). The difference between the Pi production with $K^+$ and without $K^+$ is taken as $K^+$ stimulated $H^+/K^+$-ATPase activity. The $IC_{50}$s of test compounds were calculated from each % inhibition value of compounds using the method of Litchfield-Wilcoxon (*J. Pharmacol. Exp. Ther.* (1949) 96, 99). The results are shown in Table 1.

TABLE 1

| Example | $IC_{50}$ (uM) | Example | $IC_{50}$ (uM) |
|---|---|---|---|
| 1 | 0.12 | 2 | 0.01 |
| 3 | 0.04 | 4 | 0.01 |
| 5 | 0.28 | 6 | 0.03 |
| 7 | 0.06 | 8 | 0.06 |
| 9 | 0.05 | 10 | 0.34 |
| 11 | 0.01 | 12 | 0.01 |
| 13 | 1.02 | 14 | 0.46 |
| 15 | 0.19 | 16 | 0.01 |
| 17 | 0.01 | 27 | 046 |
| 28 | 0.19 | 29 | 0.32 |
| 30 | 0.17 | 31 | 0.17 |
| 32 | 0.29 | 33 | 0.41 |
| 34 | 0.19 | 35 | 0.06 |
| 36 | 0.31 | 37 | 0.75 |
| 38 | 0.19 | 39 | 0.24 |
| 40 | 0.03 | 41 | 1.81 |

As shown in Table 1, the compounds of the present invention have excellent inhibitory effects on gastric $H^+/K^+$-ATPase.

Test Example 2. Inhibitory effects on basal gastric acid secretion in pylorus-ligated rats.

Inhibitory effects of the compounds of the present invention on basal gastric acid secretion were performed according to Shay's rat model (Shay, H., et al., 1945, gastroenterology, 5, 43-61). Male Sprague Dawley (SD) rats (200±10 g body weight) were divided into 3 groups (n=5) and fasted for 24 hours with free access to water. Control group was orally administered with 0.5% methylcellulose alone and the other groups were orally administered with test compounds suspended in 0.5% methyl-cellulose solution at doses of 1, 3 and 10 mg/kg/5 ml one hour before pylorus ligation.

Under ether anesthesia, the abdomens of the rats were incised and then the pylorus was ligated. 5 hours after ligation, the animals were sacrificed, and the gastric contents were collected. The collected contents were centrifuged at 1,000×g for 10 minutes to obtain the gastric juice. Total acid output was measured by 0.01N NaOH volume (ueq/ml) for automatic titration of the gastric juice to pH 7.0 and the $ED_{50}$s of test compounds were calculated using the Litchfield-Wilcoxon method. % inhibitory activity was calculated from the following equation and the results are shown in Table 2.

%inhibitory activity of test compound=(total acid output of control group−total acid output of the group treated with test compounds)/total acid output of control group X 100

TABLE 2

| Example | $ED_{50}$ (mg/kg) |
|---|---|
| 2 | 1.1 |
| 12 | 3.3 |
| 16 | 1.8 |
| 17 | 3.3 |

As shown in Table 2, the compounds of the present invention have potent inhibition activities against basal gastric acid secretion in pylorus-ligated rats.

TEST EXAMPLE 3

Reversible inhibition of hog gastric $H^+/K^+$-ATPase 3-1. Preparation of gastric vesicles Gastric vesicles were prepared from hog fundic mucosa using the method of Saccomani et al. (Saccomani G, Stewart H B, Shqw D, Lewin M and Sachs G, Characterization of gastric mucosal membranes. IX. Fraction and purification of K-ATPase-containing vesicles by zonal centrifugation and free-flow electrophoresis techinque. *Biochem. Biophy. Acta.* (BBA)—Biomembranes 465, 311-330, 1977.). This material was lyophilized and stored at −70° C. The protein content of gastric vesicles was determined by the Bradford method using bovine serum albumin as a standard (Bradford M M, A rapid and sensitive method for the quantitation of microgram quantities of protein utilizing the principle of protein-dye binding. *Anal Biochem.* 72, 248-254, 1976).

3-2. Determination of reversible inhibition of hog gastric $H^+/K^+$-ATPase

Activity of $H^+/K^+$-ATPase in hog microsome (lyophilized vesicle) was measured by the inorganic phosphate released from ATP using an one-step colorimetric detection method at the concentration at which the test compounds have 50% inhibition of the proton pump (Chan K M, Delfert D, and Junger K D, A direct colorimetric assay for $Ca^{2+}$-stimulated ATPase activity. *Anal Biochem*, 157, 375-380, 1986). The mode of action of test compounds on $H^+/K^+$-ATPase was investigated according to the Washout method (Beil W, Staar U, and Sewing K F, Substituted thieno[3,4-d]imidazoles, a novel group of $H^+/K^+$-ATPase inhibitors. Differentiation of their inhibition characteristics from those of omeprazole. *Eur. J. Pharmacol.*, 187, 455-67, 1990).

Lyophilized vesicle in the solution of 5 mM Pipes/Tris buffer was pre-incubated in the presence of the test compound (the compound of Example 38) at the concentration at which it has 50% inhibition of the proton pump. The previous reaction buffer was added with 2 mM $MgCl_2$, 50 mM KCl, 5 uM Valinomycin, and 0.5 mM ATP and then incubated for 30 minutes at 37° C. The $H^+/K^+$-ATPase activity was measured using the colorimetric detection method and then the test sample was centrifuged at 100,000×g for 1 hr. The vesicles are present in the form of pellets in the test sample. The supernatant thereof was replaced with the same buffer not having the test compound. The test sample was pre-incubated for 5 minutes at room temperature and then incubated further for 30 minutes at 37° C. The $H^+/K^+$-ATPase activity was also measured using the colorimetric detection method. The H+/K+-ATPase activity before washout and after washout in the test sample was analyzed, in comparison with those in the non-treated group.

As a result, the compound of Example 38 inhibited H+/K+-ATPase activity by 50% before washout and did not inhibit H+/K+-ATPase activity after washout; the gastric H+/K+-ATPase activity by the compound of Example 38 was completely recovered to non-treated group level after washout. These results confirm that the compounds of formula (I) exhibited reversible inhibition of the gastric H+/K+-ATPase.

The invention claimed is:

1. A compound of the formula (I) or a pharmaceutically acceptable salt thereof:

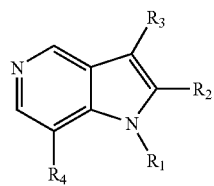

(I)

wherein:
R₁ is hydrogen; a straight or branched $C_1$-$C_6$ alkyl group, optionally substituted with one or more substituents selected from the group consisting of $C_1$-$C_5$ alkoxy, $C_3$-$C_7$ cycloalkyl, 1,3-dioxolanyl, cyano, naphthyl, $C_2$-$C_5$ alkenyloxy, and 2,3-dihydrobenzo[1,4]dioxinyl; a $C_2$-$C_6$ alkenyl group; a $C_2$-$C_6$ alkynyl group; or a benzyl group, optionally substituted with one or more substituents selected from the group consisting of halogen, $C_1$-$C_3$ alkyl, $C_1$-$C_3$ alkoxy, cyano, $C_1$-$C_3$ alkoxycarbonyl, and trifluoro-$C_1$-$C_3$ alkyl, R₂ is a straight or branched $C_1$-$C_6$ alkyl group, R₃ is hydrogen; a straight or branched $C_1$-$C_6$ alkyl group optionally substituted with hydroxyl or cyano, and R₄ is a 1,2,3,4-tetrahydroisoquinolinyl group optionally one or more substituted with halogen or $C_1$-$C_5$ alkyl; a benzyloxy group optionally one or more substituted with halogen or $C_1$-$C_5$ alkyl; or a benzylamino group optionally substituted with halogen.

2. The compound or a pharmaceutically acceptable salt thereof according to claim 1, wherein R₁ is hydrogen; a straight or branched $C_1$-$C_6$ alkyl group; a $C_1$-$C_3$ alkyl group substituted with one or more substituents selected from the group consisting of methoxy, cyclopropyl, cyclobutyl, 1,3-dioxolanyl, cyano, naphthyl, $C_2$-$C_5$ alkenyloxy, and 2,3-dihydrobenzo[1,4]dioxinyl; a $C_2$-$C_6$ alkenyl group; a $C_2$-$C_6$ alkynyl group; or a benzyl group, optionally substituted with one or more substituents selected from the group consisting of halogen, methyl, methoxy, cyano, methoxycarbonyl, and trifluoromethyl, R₂ is a methyl group, R₃ is hydrogen; a methyl group; a hydroxymethyl group; a cyanomethyl group, and R₄ is 1,2,3,4-tetrahydroisoquinolinyl; 1-methyl-6-fluoro-1,2,3,4-tetrahydroisoquinolinyl; a benzyloxy group optionally one or more substituted with halogen, or methyl; or an benzylamino group optionally substituted with one or more halogen.

3. The compound or a pharmaceutically acceptable salt thereof according to claim 1, which is selected from the group consisting of:

7-(4-fluorobenzyloxy)-2,3-dimethyl-1H-pyrrolo[3,2-c]pyridine hydrochloride;

7-(4-fluorobenzyloxy)-2,3-dimethyl-1-(prop-2-ynyl)-1H-pyrrolo[3,2-c]pyridine hydrochloride;

1-ethyl-7-(4-fluorobenzyloxy)-2,3-dimethyl-1H-pyrrolo[3,2-c]pyridine hydrochloride;

1-cyclopropylmethyl-7-(4-fluorobenzyloxy)-2,3-dimethyl-1H-pyrrolo[3,2-c]pyridine hydrochloride;

1-allyl-7-(4-fluorobenzyloxy)-2,3-dimethyl-1H-pyrrolo[3,2-c]pyridine hydrochloride;

1-(3-fluorobenzyl)-7-(4-fluorobenzyloxy)-2,3-dimethyl-1H-pyrrolo[3,2-c]pyridine hydrochloride;

7-(4-fluorobenzyloxy)-1-(3-methoxybenzyl)-2,3-dimethyl-1H-pyrrolo[3,2-c]pyridine hydrochloride;

7-(4-fluorobenzyloxy)-2,3-dimethyl-1-(4-methylbenzyl)-1H-pyrrolo[3,2-c]pyridine hydrochloride;

1-(4-fluorobenzyl)-7-(4-fluorobenzyloxy)-2,3-dimethyl-1H-pyrrolo[3,2-c]pyridine hydrochloride;

7-(4-fluorobenzyloxy)-2,3-dimethyl-1-(4-trifluoromethylbenzyl)-1H-pyrrolo[3,2-c]pyridine hydrochloride;

7-(4-fluorobenzyloxy)-1-isobutyl-2,3-dimethyl-1H-pyrrolo[3,2-c]pyridine hydrochloride;

1-benzyl-7-(4-fluorobenzyloxy)-2,3-dimethyl-1H-pyrrolo[3,2-c]pyridine hydrochloride;

1-(2,5-dimethylbenzyl)-7-(4-fluorobenzyloxy)-2,3-dimethyl-1H-pyrrolo[3,2-c]pyridine hydrochloride;

1-(2-chlorobenzyl)-7-(4-fluorobenzyloxy)-2,3-dimethyl-1H-pyrrolo[3,2-c]pyridine hydrochloride;

1-(2-fluorobenzyl)-7-(4-fluorobenzyloxy)-2,3-dimethyl-1H-pyrrolo[3,2-c]pyridine hydrochloride;

7-(4-fluorobenzyloxy)-2,3-dimethyl-1-propyl-1H-pyrrolo[3,2-c]pyridine hydrochloride;

7-(4-fluorobenzyloxy)-1-(2-methoxyethyl)-2,3-dimethyl-1H-pyrrolo[3,2-c]pyridine hydrochloride;

7-(4-chlorobenzyloxy)-2,3-dimethyl-1H-pyrrolo[3,2-c]pyridine hydrochloride;

1-benzyl-7-(4-chlorobenzyloxy)-2,3-dimethyl-1H-pyrrolo[3,2-c]pyridine hydrochloride;

7-(2,4-dichlorobenzyloxy)-2,3-dimethyl-1H-pyrrolo[3,2-c]pyridine hydrochloride;

7-benzyloxy-2,3-dimethyl-1H-pyrrolo[3,2-c]pyridine hydrochloride;

7-(2-methylbenzyloxy)-2,3-dimethyl-1H-pyrrolo[3,2-c]pyridine hydrochloride;

7-(4-fluorobenzylamino)-2,3-dimethyl-1H-pyrrolo[3,2-c]pyridine hydrochloride;

1-benzyl-7-(4-fluorobenzylamino)-2,3-dimethyl-1H-pyrrolo[3,2-c]pyridine hydrochloride;

7-benzylamino-2,3-dimethyl-1H-pyrrolo[3,2-c]pyridine hydrochloride;

2-(2,3-dimethyl-1H-pyrrolo[3,2-c]pyridin-7-yl)-6-fluoro-1-methyl-1,2,3,4-tetrahydroisoquinoline hydrochloride;

2-(2,3-dimethyl-1H-pyrrolo[3,2-c]pyridin-7-yl)-1,2,3,4-tetrahydroisoquinoline hydrochloride;

2-[1-(4-fluorobenzyl)-2,3-dimethyl-1H-pyrrolo[3,2-c]pyridin-7-yl]-1,2,3,4-tetrahydroisoquinoline hydrochloride;

1-(4-methoxycarbonylbenzyl)-7-(1,2,3,4-tetrahydroisoquinolin-2-yl)-2,3-dimethyl-1H-pyrrolo[3,2-c]pyridine hydrochloride;

2-[1-(2,3-dihydrobenzo[1,4]dioxin-6-ylmethyl)-2,3-dimethyl-1H-pyrrolo[3,2-c]pyridin-7-yl]-1,2,3,4-tetrahydroisoquinoline hydrochloride;

1-(2-methoxyethyl)-7-(1,2,3,4-tetrahydroisoquinolin-2-yl)-2,3-dimethyl-1H-pyrrolo[3,2-c]pyridine hydrochloride;

1-(2-naphthylmethyl)-7-(1,2,3,4-tetrahydroisoquinolin-2-yl)-2,3-dimethyl-1H-pyrrolo[3,2-c]pyridine hydrochloride;
1-(2-vinyloxyethyl)-7-(1,2,3,4-tetrahydroisoquinolin-2-yl)-2,3-dimethyl-1H-pyrrolo[3,2-c]pyridine hydrochloride;
1-(1,3-dioxolan-2-ylmethyl)-7-(1,2,3,4-tetrahydroisoquinolin-2-yl)-2,3-dimethyl-1H-pyrrolo[3,2-c]pyridine hydrochloride;
1-benzyl-7-(1,2,3,4-tetrahydroisoquinolin-2-yl)-2,3-dimethyl-1H-pyrrolo[3,2-c]pyridine hydrochloride;
1-isobutyl-7-(1,2,3,4-tetrahydroisoquinolin-2-yl)-2,3-dimethyl-1H-pyrrolo[3,2-c]pyridine hydrochloride;
1-cyclobutylmethyl-7-(1,2,3,4-tetrahydroisoquinolin-2-yl)-2,3-dimethyl-1H-pyrrolo[3,2-c]pyridine hydrochloride;
2-(2,3-dimethyl-1-propyl-1H-pyrrolo[3,2-c]pyridin-7-yl)-1,2,3,4-tetrahydroisoquinoline hydrochloride;
2-(1-cyclopropylmethyl-2,3-dimethyl-1H-pyrrolo[3,2-c]pyridin-7-yl)-1,2,3,4-tetrahydroisoquinoline hydrochloride;
2-(1-ethyl-2,3-dimethyl-1H-pyrrolo[3,2-c]pyridin-7-yl)-1,2,3,4-tetrahydroisoquinoline hydrochloride;
3-[7-(3,4-dihydro-1H-isoquinolin-2-yl)-2,3-dimethylpyrrolo[3,2-c]pyridin-1-ylmethyl]-benzonitrile hydrochloride;
[7-(3,4-dihydro-1H-isoquinolin-2-yl)-2,3-dimethylpyrrolo[3,2-c]pyridin-1-yl]-acetonitrile hydrochloride;
1-benzyl-7-(1,2,3,4-tetrahydroisoquinolin-2-yl)-3-hydroxymethyl-2-methyl-1H -pyrrolo[3,2-c]pyridine hydrochloride
2-(1-benzyl-2-methyl-1H-pyrrolo[3,2-c]pyridin-7-yl)-1,2,3,4-tetrahydroisoquinoline hydrochloride; and
1-benzyl-7-(3,4-dihydro-1H-isoquinolin-2-yl)-2-methyl-1H-pyrrolo[3,2-c]pyridin-3-carbonitrile hydrochloride.

4. The compound or a pharmaceutically acceptable salt thereof according to claim 3, which is selected from the group consisting of:

7-(4-fluorobenzyloxy)-2,3-dimethyl-1H-pyrrolo[3,2-c]pyridine hydrochloride;
7-(4-fluorobenzyloxy)-2,3-dimethyl-1-(prop-2-ynyl)-1H-pyrrolo[3,2-c]pyridine hydrochloride;
1-ethyl-7-(4-fluorobenzyloxy)-2,3-dimethyl-1H-pyrrolo[3,2-c]pyridine hydrochloride;
1-cyclopropylmethyl-7-(4-fluorobenzyloxy)-2,3-dimethyl-1H-pyrrolo[3,2-c]pyridine hydrochloride;
1-allyl-7-(4-fluorobenzyloxy)-2,3-dimethyl-1H-pyrrolo[3,2-c]pyridine hydrochloride;
1-(3-fluorobenzyl)-7-(4-fluorobenzyloxy)-2,3-dimethyl-1H-pyrrolo[3,2-c]pyridine hydrochloride;
7-(4-fluorobenzyloxy)-1-(3-methoxybenzyl)-2,3-dimethyl-1H-pyrrolo[3,2-c]pyridine hydrochloride;
7-(4-fluorobenzyloxy)-2,3-dimethyl-1-(4-methylbenzyl)-1H-pyrrolo[3,2-c]pyridine hydrochloride;
1-(4-fluorobenzyl)-7-(4-fluorobenzyloxy)-2,3-dimethyl-1H-pyrrolo[3,2-c]pyridine hydrochloride;
7-(4-fluorobenzyloxy)-2,3-dimethyl-1-(4-trifluoromethylbenzyl) -1H-pyrrolo[3,2-c]pyridine hydrochloride;
7-(4-fluorobenzyloxy)-1-isobutyl-2,3-dimethyl-1H-pyrrolo[3,2-c]pyridine hydrochloride;
1-benzyl-7-(4-fluorobenzyloxy)-2,3-dimethyl-1H-pyrrolo[3,2-c]pyridine hydrochloride;
1-(2,5-dimethylbenzyl)-7-(4-fluorobenzyloxy)-2,3-dimethyl-1H-pyrrolo[3,2-c]pyridine hydrochloride;
1-(2-chlorobenzyl)-7-(4-fluorobenzyloxy)-2,3-dimethyl-1H-pyrrolo[3,2-c]pyridine hydrochloride;
1-(2-fluorobenzyl)-7-(4-fluorobenzyloxy)-2,3-dimethyl-1H-pyrrolo[3,2-c]pyridine hydrochloride;
7-(4-fluorobenzyloxy)-2,3-dimethyl-1-propyl-1H-pyrrolo[3,2-c]pyridine hydrochloride;
7-(4-fluorobenzyloxy)-1-(2-methoxyethyl)-2,3-dimethyl-1H-pyrrolo[3,2-c]pyridine hydrochloride;
2-(2,3-dimethyl-1H-pyrrolo[3,2-c]pyridin-7-yl)-1,2,3,4-tetrahydroisoquinoline hydrochloride;
2-[1-(4-fluorobenzyl)-2,3-dimethyl-1H-pyrrolo[3,2-c]pyridin-7-yl]-1,2,3,4-tetrahydroisoquinoline hydrochloride;
1-(4-methoxycarbonylbenzyl)-7-(1,2,3,4-tetrahydroisoquinolin-2-yl)-2,3-dimethyl-1H-pyrrolo[3,2-c]pyridine hydrochloride;
2-[1-(2,3-dihydrobenzo[1,4]dioxin-6-ylmethyl)-2,3-dimethyl-1H-pyrrolo[3,2-c]pyridin-7-yl]-1,2,3,4-tetrahydroisoquinoline hydrochloride;
1-(2-methoxyethyl)-7-(1,2,3,4-tetrahydroisoquinolin-2-yl)-2,3-dimethyl-1H-pyrrolo[3,2-c]pyridine hydrochloride;
1-(2-naphthylmethyl)-7-(1,2,3,4-tetrahydroisoquinolin-2-yl)-2,3-dimethyl-1H-pyrrolo[3,2-c]pyridine hydrochloride;
1-(2-vinyloxyethyl)-7-(1,2,3,4-tetrahydroisoquinolin-2-yl)-2,3-dimethyl-1H-pyrrolo[3,2-c]pyridine hydrochloride;
1-(1,3-dioxolan-2-ylmethyl)-7-(1,2,3,4-tetrahydroisoquinolin-2-yl)-2,3-dimethyl-1H-pyrrolo[3,2-c]pyridine hydrochloride;
1-benzyl-7-(1,2,3,4-tetrahydroisoquinolin-2-yl)-2,3-dimethyl-1H-pyrrolo[3,2-c]pyridine hydrochloride;
1-isobutyl-7-(1,2,3,4-tetrahydroisoquinolin-2-yl)-2,3-dimethyl-1H-pyrrolo[3,2-c]pyridine hydrochloride;
1-cyclobutylmethyl-7-(1,2,3,4-tetrahydroisoquinolin-2-yl)-2,3-dimethyl-1H-pyrrolo[3,2-c]pyridine hydrochloride;
2-(2,3-dimethyl-1-propyl-1H-pyrrolo[3,2-c]pyridin-7-yl)-1,2,3,4-tetrahydroisoquinoline hydrochloride;
2-(1-cyclopropylmethyl-2,3-dimethyl-1H-pyrrolo[3,2-c]pyridin-7-yl)-1,2,3,4-tetrahydroisoquinoline hydrochloride;
2-(1-ethyl-2,3-dimethyl-1H-pyrrolo[3,2-c]pyridin-7-yl)-1,2,3,4-tetrahydroisoquinoline hydrochloride; and
3-[7-(3,4-dihydro-1H-isoquinolin-2-yl)-2,3-dimethylpyrrolo[3,2-c]pyridin-1-ylmethyl]-benzonitrile hydrochloride.

5. The compound or a pharmaceutically acceptable salt thereof according to claim 4, which is selected from the group consisting of:

7-(4-fluorobenzyloxy)-2,3-dimethyl-1-(prop-2-ynyl)-1H-pyrrolo[3,2-c]pyridine hydrochloride;
1-cyclopropylmethyl-7-(4-fluorobenzyloxy)-2,3-dimethyl-1H-pyrrolo[3,2-c]pyridine hydrochloride;
1-(3-fluorobenzyl)-7-(4-fluorobenzyloxy)-2,3-dimethyl-1H-pyrrolo[3,2-c]pyridine hydrochloride;
7-(4-fluorobenzyloxy)-2,3-dimethyl-1-(4-methylbenzyl)-1H-pyrrolo[3,2-c]pyridine hydrochloride;
1-benzyl-7-(4-fluorobenzyloxy)-2,3-dimethyl-1H-pyrrolo[3,2-c]pyridine hydrochloride;
7-(4-fluorobenzyloxy)-2,3-dimethyl-1-propyl-1H-pyrrolo[3,2-c]pyridine hydrochloride;
7-(4-fluorobenzyloxy)-1-(2-methoxyethyl)-2,3-dimethyl-1H-pyrrolo[3,2-c]pyridine hydrochloride; and
2-(2,3-dimethyl-1-propyl-1H-pyrrolo[3,2-c]pyridin-7-yl)-1,2,3,4-tetrahydroisoquinoline hydrochloride.

6. A process for preparing a compound of formula (I) or a pharmaceutically acceptable salt thereof, which comprises:

reacting a compound of formula (II) with $R_4$—H to obtain a compound of formula (III), reacting a compound of formula (III) with a compound of formula (IV) to obtain a compound of formula (Ia), and reacting the compound of formula (Ia) with $R_1$—X to obtain a compound of formula (I):

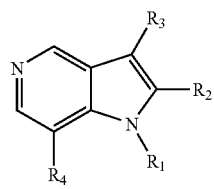
(I)

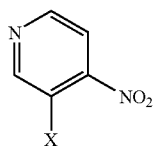
(II)

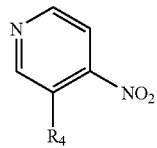
(III)

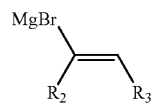
(IV)

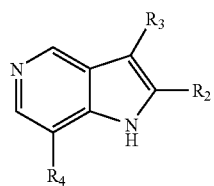
(Ia)

wherein, $R_1$, $R_2$, $R_3$, and $R_4$ are the same as defined in claim 1 and X is halogen.

7. A pharmaceutical composition comprising a therapeutically effective amount of any of the compound of formula (I) or a pharmaceutically acceptable salt thereof according to claim 1 and a pharmaceutically acceptable carrier.

\* \* \* \* \*